(12) United States Patent
Stout

(10) Patent No.: US 7,955,347 B2
(45) Date of Patent: Jun. 7, 2011

(54) LOW COST SAFETY LANCET

(75) Inventor: Jeffrey T. Stout, Smyrna, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 352 days.

(21) Appl. No.: 11/570,195

(22) PCT Filed: Jun. 24, 2005

(86) PCT No.: PCT/US2005/022739
§ 371 (c)(1),
(2), (4) Date: Dec. 7, 2006

(87) PCT Pub. No.: WO2006/004664
PCT Pub. Date: Jan. 12, 2006

(65) Prior Publication Data
US 2007/0185515 A1    Aug. 9, 2007

Related U.S. Application Data

(60) Provisional application No. 60/582,867, filed on Jun. 25, 2004.

(51) Int. Cl.
*A61B 17/32* (2006.01)
(52) U.S. Cl. .......................................... 606/181
(58) Field of Classification Search .................. 606/181, 606/182; 604/136; 600/583, 573
See application file for complete search history.

(56) References Cited

U.S. PATENT DOCUMENTS

| | | | |
|---|---|---|---|
| 4,375,815 A | 3/1983 | Burns | |
| 4,527,561 A | 7/1985 | Burns | |
| 4,983,178 A * | 1/1991 | Schnell | 606/181 |
| 5,133,730 A * | 7/1992 | Biro et al. | 606/182 |
| 5,304,192 A * | 4/1994 | Crouse | 606/181 |
| 5,421,347 A * | 6/1995 | Enstrom | 600/567 |
| 5,554,166 A | 9/1996 | Lange et al. | |
| 5,571,132 A | 11/1996 | Mawhirt et al. | |
| 5,628,764 A | 5/1997 | Schraga | |
| 5,707,384 A | 1/1998 | Kim | |
| 5,755,733 A * | 5/1998 | Morita | 606/182 |
| 5,908,434 A | 6/1999 | Schraga | |
| 6,042,595 A * | 3/2000 | Morita | 606/181 |
| 6,343,797 B1 | 2/2002 | Tajnafoi et al. | |
| 6,866,641 B2 * | 3/2005 | Marshall | 600/583 |
| 6,945,982 B2 * | 9/2005 | Marshall et al. | 606/182 |
| 2002/0087180 A1 * | 7/2002 | Searle et al. | 606/181 |
| 2003/0130597 A1 * | 7/2003 | Marshall | 600/583 |
| 2003/0158568 A1 * | 8/2003 | Marshall et al. | 606/181 |
| 2004/0098008 A1 * | 5/2004 | Taylor et al. | 606/181 |
| 2004/0102802 A1 * | 5/2004 | Marshall | 606/182 |

* cited by examiner

*Primary Examiner* — Anhtuan T Nguyen
*Assistant Examiner* — David Eastwood
(74) *Attorney, Agent, or Firm* — Gardner Groff Greenwald & Villanueva, PC

(57) ABSTRACT

A lancing device has a housing, an activation/retraction control assembly, and a lancet. The control assembly and the housing have cooperating engagement structures such as detents that disengage after a predetermined launch force is applied to the control assembly. In this way, the lancet is driven to its puncturing position without the use of a drive spring. In addition, the control assembly and the lancet have cooperating releasable engagement structures such as notched sections and tamped protrusions that disengage when the lancet reaches its puncturing position, thereby freeing the lancet from the control assembly. And the control assembly has angled retraction structures that engage the freed lancet to bias it back safely into the housing.

10 Claims, 11 Drawing Sheets

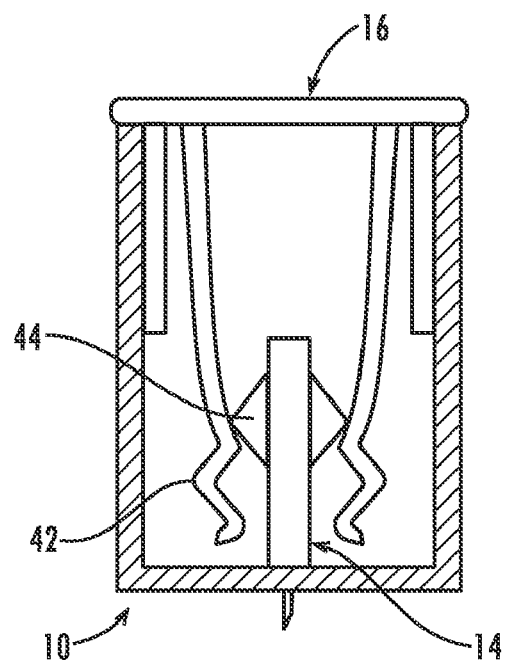
Fig. 5
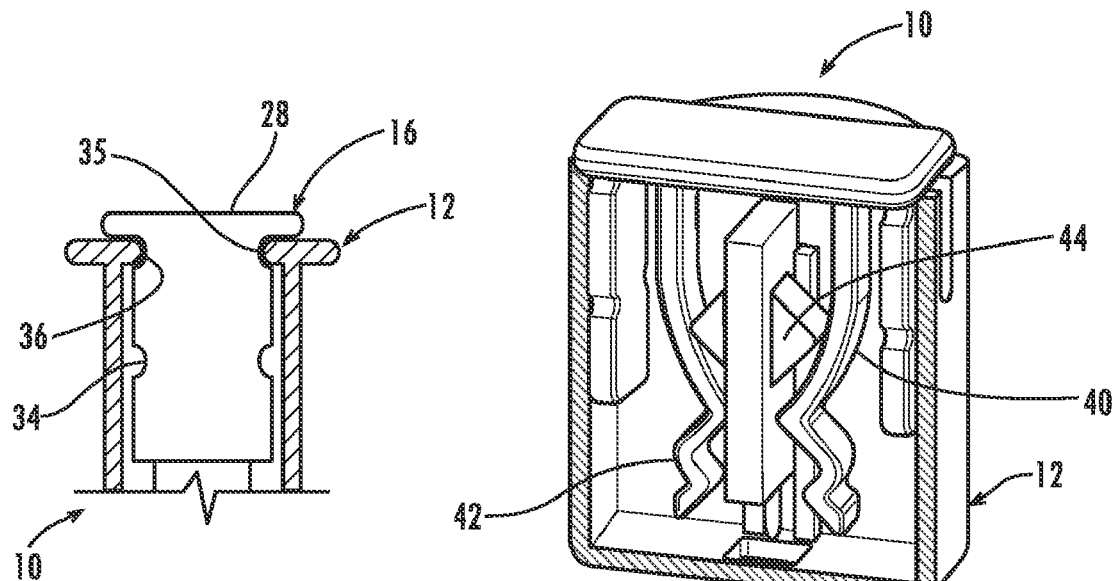
Fig. 6
Fig. 7

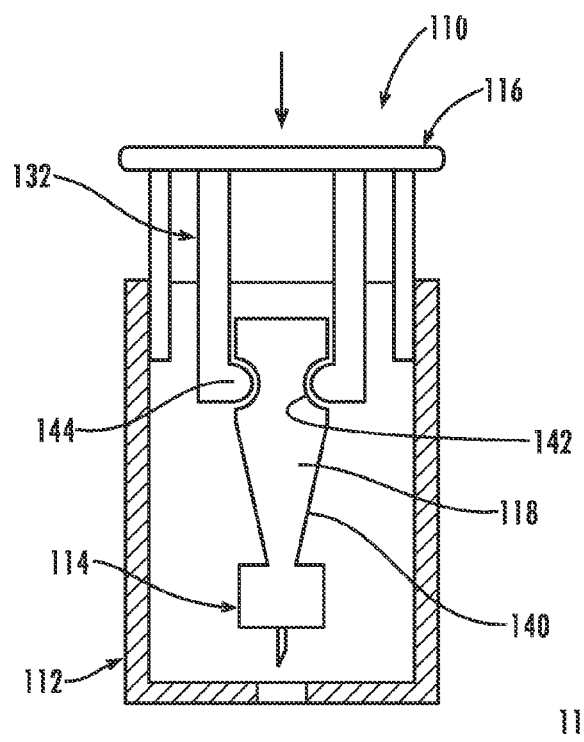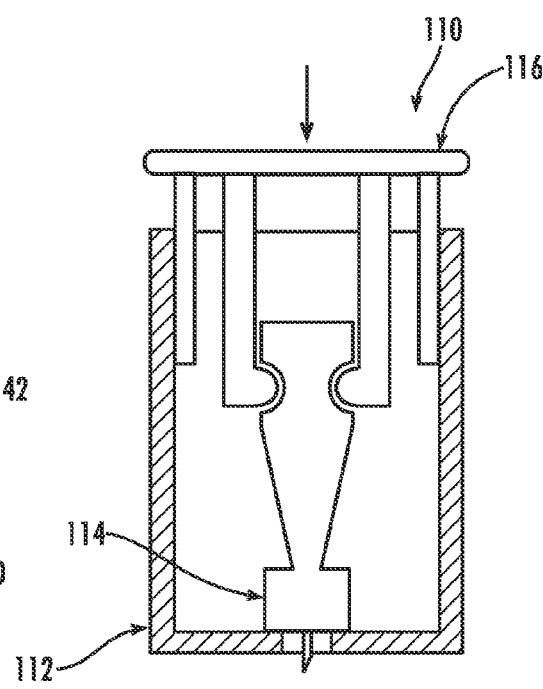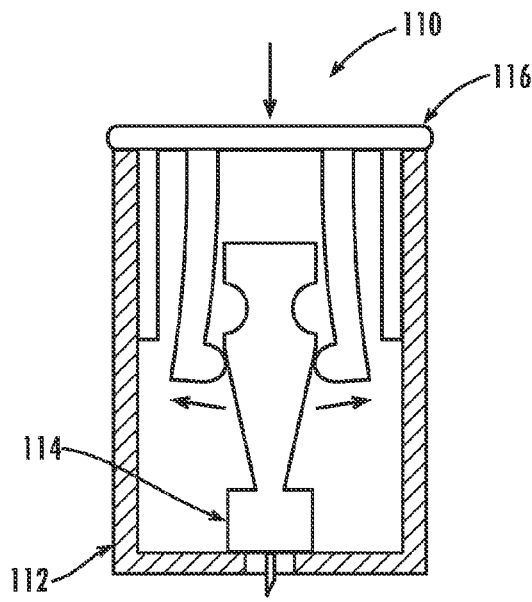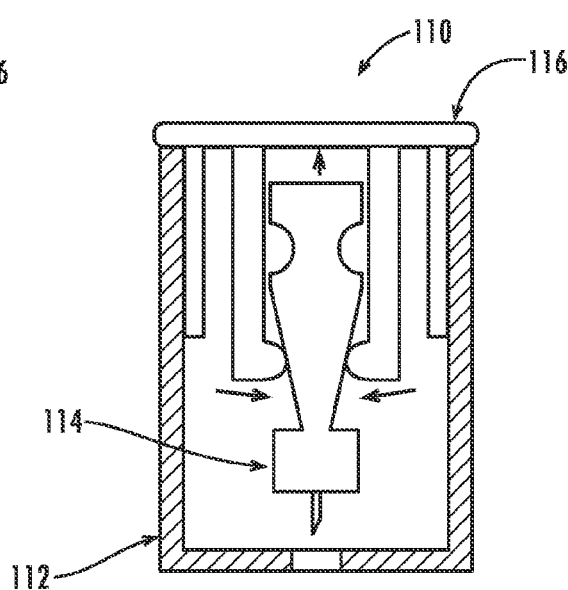

LOW COST SAFETY LANCET

CROSS REFERENCE TO RELATED APPLICATION

This application claims the priority benefit of U.S. Provisional Patent Application Ser. No. 60/582,867 filed on Jun. 25, 2004, which is hereby incorporated herein by reference in its entirety for all purposes.

TECHNICAL FIELD

The present invention relates generally to medical devices and, more particularly, to a lancing device for penetrating the skin of a human or animal subject for sampling of blood and/or other body fluids.

BACKGROUND OF THE INVENTION

Lancing devices are used to penetrate the skin of a subject and obtain a sample of blood or other body fluid, as in the testing of blood sugar levels by diabetics. Typically, a lancet having a sharp point is translationally mounted within a housing portion of a lancing device. The lancet is driven by a spring or other biasing means to cause the sharp point to extend a small distance through an opening in the housing and into the subject's skin, creating a wound from which the sample of body fluid is collected. The housing optionally includes a pressure surface for "pumping" the wound to enhance sample size, and may also incorporate a capillary tube or other sample collection media. The endcap of the housing or a portion of the housing adjacent the lancet opening may include an open window or a transparent section for viewing the sample collection site, and may also include one or more sample size indicators for comparing the size of a sample to a desired sample size. Example lancing devices are shown in U.S. Pat. No. 5,356,420; U.S. Pat. No. 5,397,334; and U.S. Pat. No. 5,439,473, all of which are hereby incorporated herein by reference.

Lancing devices typically are intended either for a single use or for multiple uses. Single-use lancing devices generally are disposed of after one use. For example, in a hospital or clinic, it is desirable to provide a single-use lancing device that can be used on a patient and then disposed of to eliminate any risk of infection to subsequent patients or caregivers from exposure to residual body fluids remaining on the lancing device. Accordingly, single-use lancing devices oftentimes include a disabling mechanism to prevent accidental or intentional re-use of the device. Various forms of disabling mechanisms are available, and are well known in the art. For example, the disabling mechanism may comprise a return spring for retracting the sharp point of the lancet back into the housing after a single use, break-away elements or a frangible link in the cocking or triggering mechanism to prevent re-arming or re-firing the device after a single use, a locking element, and/or a shield for blocking travel of the lancet.

Because single-use lancing devices normally are disposed of after one use, they generally are relatively simple in construction so that they can be economically manufactured in large quantities. However, most known single-use lancing devices are too costly and/or are not true safety lancets. For example, many single-use lancing devices include a housing, a lancet having a body and a tip, a drive spring for propelling the lancet, an actuator for firing the drive spring, and a retraction spring and disabling mechanism to prevent reuse of the lancing device. With this number of parts, the cost of the lancing device is higher than most users desire. And some other single-use lancing devices eliminate the retraction spring and disabling mechanism to reduce cost. But then these lancing devices permit reuse, so they are not true safety lancets.

Accordingly, a need exists for lancing devices that are simple in construction and therefore low in cost. In addition, it would be desirable for such lancing devices to include disabling means so that they cannot be reused. It is to the provision of lancing devices meeting these and other needs that the present invention is primarily directed.

SUMMARY OF THE INVENTION

Briefly described, the present invention provides a lancing device having a housing, an activation/retraction control assembly, and a lancet. The lancet has a body, a puncturing tip that extends from the body, and a removable sterility cap the covers the tip. The housing has a lancing opening through which the puncturing tip extends in its fully extended position to puncture the skin. And the activation/retraction control assembly includes structures that operate to drive the lancet from a ready position to the fully extended position, and then to retract the lancet so that the tip is back inside the housing.

Preferably, these three components include all of the structural features of the lancing device, so no other parts are needed. In addition, these three components preferably are made of molded plastic and can be easily assembled together. In this way, the lancing device provides a reliable safety lancet that is very inexpensive to produce.

The control assembly and the housing have cooperating engagement structures that hold the control assembly in place relative to the housing in the ready position. When a predetermined launch force is applied to a pressing member of the control assembly, the cooperating engagement structures disengage, and the control assembly and the lancet are thus launched in the lancing stroke. The predetermined force is large enough to overcome the resistive force of the cooperating engagement structures and launch the lancet with enough force to ensure that it travels all the way to the fully extended position. In this way, the lancet is driven to its puncturing position without the use of a drive spring.

In addition, the control assembly and the lancet have cooperating releasable engagement structures that hold the lancet to the control assembly when the lancet is driven from the ready position to the fully extended position. But when the lancet is stopped at its fully extended puncturing position, the cooperating releasable engagement structures disengage as the launch force drives the control assembly free of the lancet. The freed control assembly continues moving forward until it is stopped, and then its angled retraction structures engage and retract the lancet so that its puncturing tip is safely within the housing.

In a first example embodiment, the cooperating engagement structures are provided by detents on the housing inner walls and on control arms extending from the pressing member of the control assembly. In addition, the lancing device may include a second detent or other engagement structure for holding the control assembly in its fully depressed position, to prevent retracting the control assembly and reusing the lancing device.

The cooperating releasable engagement structures are provided by notched sections of control fingers that extend from the pressing member of the control assembly, and ramped protrusions on the body of the lancet. The notched sections receive and hold the ramped protrusions so that the lancet and the control assembly move together when the control assembly it depressed and launched. But when the lancet is stopped in the fully extended position with the control member being free to continue moving forward, the notched sections are driven downward along the ramped protrusion. This forces the notched sections outward as they move downward, in the process storing a charge in the control fingers, until they are past the outermost part of the ramped protrusions. Now the notched sections are disengaged from the ramped protrusions, which disables the lancing device from reuse. When the control assembly reaches its fully depressed position, it is held in there by the second engagement structure. The angled retraction structures are provided by angled sections of the control fingers, and they are now engaged with the ramped protrusions. The angled sections of the charged control fingers then bias the lancet back up until the tip is back inside the housing.

In a second example embodiment, the releasable engagement structures are switched between the control assembly and the lancet. In other words, the notched sections are defined by the lancet body and the ramped protrusions are defined by the control fingers, instead of vice versa. In addition, the angled retraction sections are defined by the lancet body instead of the control fingers. Nevertheless, in this configuration the lancing device operates in substantially the same way as the first embodiment does.

In a third example embodiment, the ramped protrusions together have the shape of an inverted heart or letter "V". And in a fourth example embodiment, the ramped protrusions together are delta-shaped. In these configurations, each of the ramped protrusions are generally wedge-shaped and have lock surfaces that prevent the lancet from being pulled from engagement with the control assembly when the user pulls the sterility cap off for use.

Accordingly, the lancing device may be provided as three (or another small number) pieces of plastic that are easily assembled together. And the lancing device does not need a drive spring, as conventional lancing devices do. In this way, the lancing device is very inexpensive to manufacture as a single-use disposable unit. In addition, the lancing device retracts the lancet after use and is disabled from reuse, so it is a true safety lancet.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWING FIGURES

FIG. 5 is a side view of the lancing device of FIG. 2, showing the activation/retraction control assembly stopped after disengaging from the lancet and continuing to travel after the lancet stopped.

FIG. 6 is a right side view of an upper portion of the lancing device of FIG. 5 with a right sidewall of the housing cutaway.

FIG. 7 is a perspective view of the lancing device of FIG. 2, showing the lancet retracted by the activation/retraction control assembly back into the housing.

FIG. 8 is a side view of a lancing device according to a second example embodiment of the invention, showing the activation/retraction control assembly being pressed to activate the lancing device.

FIG. 9 is a side view of the lancing device of FIG. 8, showing the lancet stopped in a fully extended position for puncturing, and the activation/retraction control assembly free to continue traveling.

FIG. 10 is a side view of the lancing device of FIG. 8, showing the activation/retraction control assembly stopped.

FIG. 11 is a side view of the lancing device of FIG. 8, showing the lancet retracted by the activation/retraction control assembly back into the housing.

DETAILED DESCRIPTION OF EXAMPLE EMBODIMENTS

Figure 1:
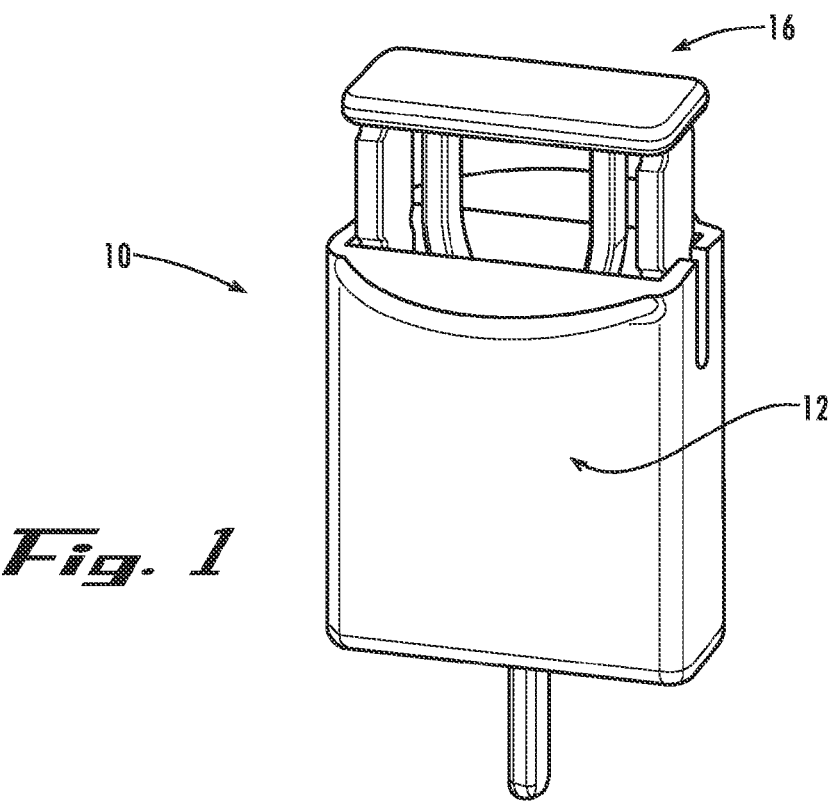
FIG. 1 is a perspective view of a lancing device according to a first example embodiment of the invention.
Figure 2:
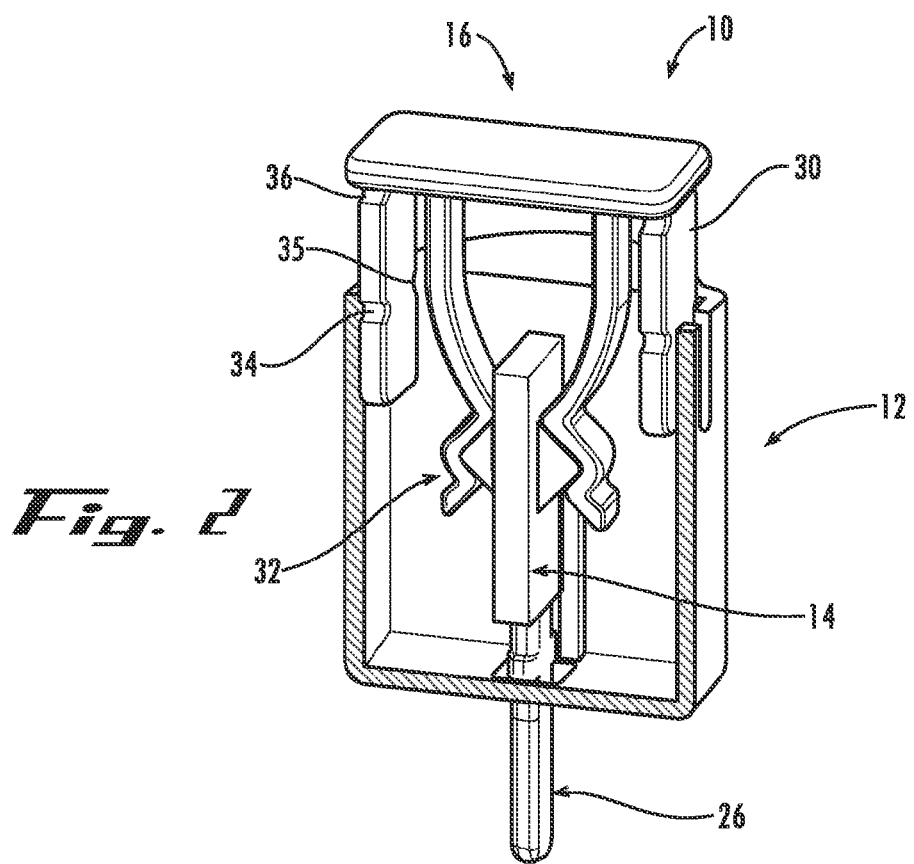
FIG. 2 is a perspective view of the lancing device of FIG. 1 with a front sidewall of the housing cutaway, showing the lancing device in a ready position.

The present invention may be understood more readily by reference to the following detailed description of example embodiments taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a", "an", and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about", it will be understood that the particular value forms another embodiment.

Referring now to the drawings, FIGS. 1-6 show a lancing device 10 according to a first example embodiment of the present invention. The lancing device 10 is a single use, disposable device. In alternative embodiments, the lancing device is adapted to accept replaceable lancets for use as a reusable lancing device.

The lancing device 10 includes a housing 12, a lancet 14, and an activation/retraction control assembly 16. Preferably, each of these components is a single piece, so that the entire lancing device 10 consists of only three parts, thereby keeping its cost low. Alternatively, the control assembly 16 may be manufactured integrally as part of the housing 12 or the lancet 14, with thin-walled zones for breaking into separate parts during use. Of course, the lancing device 10 may be configured with additional components, or with these components made of multiple pieces (e.g., with a plastic lancet body and a metal lancet needle), if desired.

In the depicted embodiment, the housing 12 is a single piece molded of plastic having four sidewalls and a bottom/distal wall forming an interior space with an open top/proximal end. In addition, the housing 12 has two flanges adjacent the open top end that extend outwardly for positioning the user's fingers during use. The lancet 14 includes a body 18 and a sharp puncturing end 20. The lancet body 18 is movable along a guide structure 22, for example, two ridges on each of the opposing front and back sidewalls of the housing 12 that define a channel that receives the lancet body (see FIG. 4). Alternatively, the guide structure may be provided by one ridge on each sidewall that is received in a slot in each side of the lancet body, one groove in each sidewall that receives the lancet body, etc. The lancing device 10 is operable to extend the lancet puncturing end 20 through a lancing opening 24 in the bottom wall of the housing 12 to puncture the user's skin. During shipping and storage, the puncturing end 20 is covered by a sterility cap 26 that is easily removed to use the lancing device 10.

Generally described, the control assembly 16 and the housing 12 have at least one first set of cooperating engagement structures 34 and 35 for holding the control assembly in a ready position. Preferably, the control assembly 16 and/or the housing 12 also has at least one second cooperating engagement structure 36 for holding the control assembly in a finished position after the lancing stroke. Preferably, the second cooperating engagement structure 36 engages one of the first cooperating engagement structures 35 to hold the control assembly in the finished position, but a separate set of second cooperating engagement structures may be provided, if so desired. In addition, the control assembly 16 and the lancet 14 have at least one set of cooperating releasable engagement structures 42 and 44 for releasably holding the lancet to the control assembly during the lancing stroke. And the control assembly 16 has at least one angled retraction structure 40 for retracting the lancet after the lancing stroke.

The control assembly 16 is configured for launching the lancet 14, but only after a predetermined amount of force has been applied by the user to overcome the resistive force of the first cooperating engagement structures 34 and 35. The control assembly 16 is configured so that the required launch force is large enough that, once launched, the control assembly drives the lancet 14 into the skin and all the way to its fully extended position. In addition, the control assembly 16 is configured so that the required launch force is also large enough that, once the lancet 14 is stopped in its fully extended position, the releasable engagement structures 42 and 44 disengage and the control assembly continues to travel to its finished position. Preferably, when the control assembly 16 is stopped in its finished position, the second cooperating engagement structure 36 is engaged by one of the first cooperating engagement structures 35 to hold the control assembly from being pulled out of the housing 12 to reuse the lancing device 10. Now the control assembly 16 and the lancet 14 are in relative positions so that the angled retraction structure 40 biases the lancet 14 back into the housing 12 so that the lancing device 10 cannot be reused.

In the depicted embodiment, the activation/retraction control assembly 16 is a single piece molded of plastic having a pressing member 28 with two (or another number of) launch control arms 30 and two (or another number of) resilient lancet control fingers 32 extending downward into the interior space of the housing 12. The pressing member 28 provides a surface for the user to depress with a finger or palm of the hand, and preferably is sized and shaped to cover the open top of the housing 12. The launch control arms 30 and the housing 12 include the first set of cooperating engagement structures 34 and 35 (see FIGS. 2 and 6). If desired, slots 38 may be provided in the housing 12 (and/or in the launch control arms 30) for permitting slight deflection to facilitate disengagement of the engagement structures 34 and 35 upon depression of the pressing member 28.

In a typical commercial embodiment, the cooperating engagement structures 34, 35, and 36 are detents defined by the launch control arms 30 and the housing 12, respectively. For example, the engagement structures 34 may be female detents in the launch control arms 30 and the engagement structures 35 may be male detents on the housing 12, or vice versa. And the engagement structures 36 may be female detents in the launch control arms 30, similar to and spaced apart from the female detent engagement structures 34. Alternatively, the cooperating engagement structures 34, 35, and 36 may be provided by other conventional structures and/or in other quantities selected for carrying out the purposes described herein. In one such alternative embodiment, the cooperating engagement structures 34 and 35 are provided by thin-walled zones that fail under the launch force when the pressing member 28 is depressed. And, of course, the engagement structures 34 and 36 may be defined by the housing 12 and the engagement structures 35 defined by the launch control arms 30, if desired.

In addition, the depicted embodiment has the cooperating releasable engagement structures 42 and 44 provided by notched sections of the lancet control fingers 32 and ramped protrusions on the lancet body 18, respectively. The notched sections 42 and the protrusions 44 are configured so that they are held together and travel together until the lancet 14 is stopped in the fully extended position, at which time the notches slide down the ramped protrusions, which pushes apart the resilient lancet control fingers 32, until the notches are past the protrusions, leaving the control assembly 16 free to continue traveling. Furthermore, the angled retraction structures 40 are provided by angled sections of the lancet control fingers 32. The angled sections 40, which are now resiliently deflected outwardly, push inwardly (to their neutral position) against the protrusions 44, which biases the lancet 14 upward and retracts it into the housing 12 after puncturing the skin. Alternatively, the cooperating releasable engagement structures 42 and 44 and the angled retraction structures 40 may be provided by other conventional structures and/or in other quantities selected for carrying out the purposes described herein. In one such alternative embodiment, the cooperating releasable engagement structures 42 and 44 are provided by a plurality of detents configured to withstand the launch force when the lancet 14 enters the skin but to give and disengage when the lancet is stopped in the fully extended position. In another alternative embodiment, the cooperating releasable engagement structures 42 and 44 include thin-walled zones that fail under the launch force when the lancet 14 is stopped.

Figure 3:
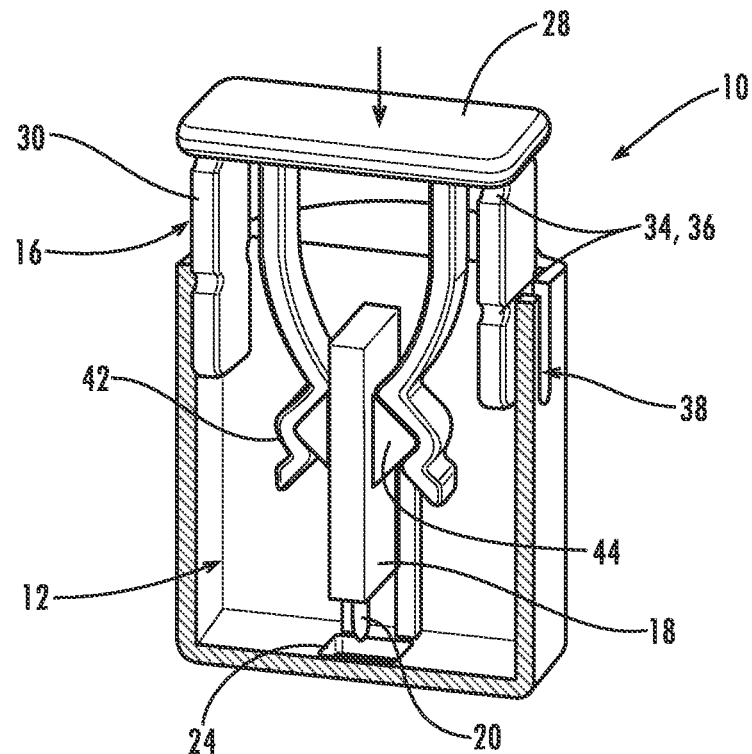
FIG. 3 is a perspective view of the lancing device of FIG. 2, showing the sterility cap removed and the activation/retraction control assembly being pressed to activate the lancing device.

The operation of the lancing device 10 will now be described. FIG. 3 shows the lancing device 10 being activated. The user positions the bottom wall of the housing 12 against the skin at the location where lancing is desired, the depresses the pressing member 28 with a finger or the palm of a hand. Because of the restraining engagement of the first cooperating engagement structures 34 and 35, the control assembly 16 does not readily move relative to the housing 12. The user must apply a predetermined amount of force to the pressing member 28 sufficient to overcome the resistive force of the engaged detent structures 34 and 35. Once this predetermined force is applied, the control assembly 16 moves rapidly downward, with the engagement of the notched sections 42 of the lancet control fingers 32 and the ramped protrusions 44 of the lancet body 18 forcing the lancet 16 rapidly downward too.

Figure 4:
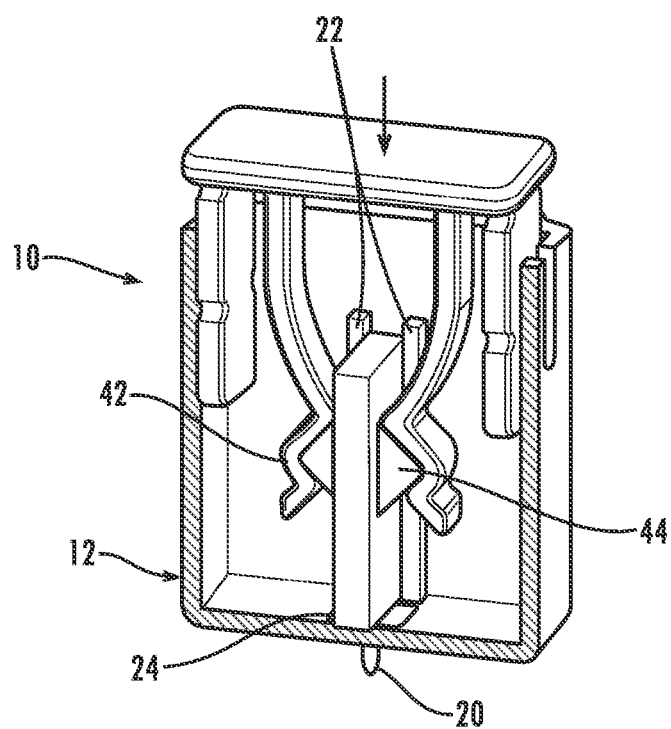
FIG. 4 is a perspective view of the lancing device of FIG. 2, showing the lancet activated and stopped in a fully extended position for puncturing.

Referring to FIG. 4, the lancet 14 travels downward until the distal face of the lancet body 18 contacts and is stopped by the inside face of the bottom wall of the housing 12. This stops the travel of the lancet 14 in the fully extended position, with the lancet puncturing end 20 extending through the housing's lancing opening 24 and puncturing the skin.

In this way, the lancet 14 is driven manually by the energy of the user, without a drive spring. This innovative design reduces the number of parts and the size of the lancing device 10, contributing to a lower cost of manufacture.

The predetermined force required to overcome the detents 34 and 35 is selected to be large enough that, after the lancet 14 has been stopped, the residual force is sufficient to overcome the resistive force of the engaged notched sections 42 and protrusions 44. With the lancet 14 stopped in its fully extended position shown in FIG. 4, the notched sections 42 disengage from the protrusions 44 as the control assembly 16 continues traveling downward to its stop position shown in FIG. 5. The control assembly 16 is then stopped, for example, by the pressing member 28 contacting the housing 12.

The control assembly 16 is now held in its stopped position by the restraining engagement of the second detent engagement structures 36 and the first detent engagement structures 35, as shown in FIGS. 5 and 6. So now the biasing engagement of the inwardly faced angled surfaces of the angled sections 40 of the control assembly 16 with the ramped protrusions 44 on the lancet body 18 retracts the lancet 14 back into the housing 12. And the resistive force of the engaged detent structures 36 and 35 holds the control assembly 16 in place depressed into the housing 12. In this way, the lancing device 10 is disabled so that it cannot be reused, resulting in a true safety lancet.

In alternative embodiments, the activation/retraction control assembly 16 may be provided with the releasable engagement structures 42 and 44 and the retraction structure 40 in other configurations for achieving substantially the same result of activating the lancet and then retracting it so that the lancing device is disabled. For example, the notches and ramped protrusions of the control fingers and the lancet body may be switched, and the angled sections may be provided on the lancet body instead of on the control fingers to accomplish the inventive concept of the present invention.

FIG. 8 shows a lancing device according to a second example embodiment of the invention that implements this same inventive concept. The lancing device 110 has a housing 112, a lancet 114, and an activation/retraction control assembly 116. In this embodiment, the lancet control fingers 132 include the ramped protrusions 144 and the lancet body 118 includes the notched sections 142 and the angled sections 140.

FIGS. 8-11 show the operation of the lancing device 110, which occurs in substantially the same fashion as the operation of the lancing device 10 of the first embodiment. In FIG. 8, the activation/retraction control assembly 116 is being pressed to activate the lancing device. In FIG. 9, the lancet 114 is stopped in a fully extended position for puncturing, and the control assembly 116 is free to continue traveling. In FIG. 10, the control assembly 116 is stopped. And in FIG. 11, the lancet 114 is retracted by the control assembly 116 back into the housing 112.

Figure 12:
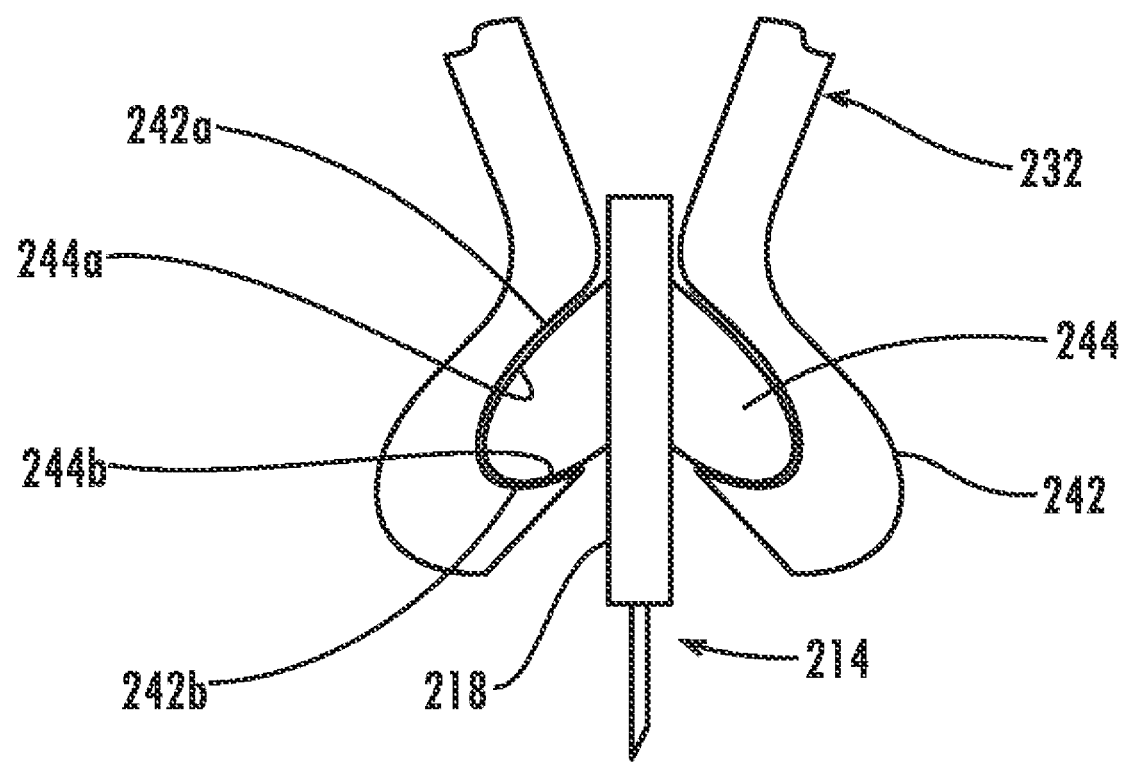
FIG. 12 is a side detailed view of the interrelationship of the lancet and the control assembly of a lancing device according to a third example embodiment of the invention.

FIG. 12 shows part of a lancing device according to a third example embodiment of the invention that is similar to the first example embodiment. In this embodiment, however, the lancet body 218 includes ramped protrusions 244 that together have the general shape of an inverted "V" or heart. And the lancet control fingers 232 have two notched sections 242 that cooperatively conform generally to the shape of the ramped protrusions 244. In other words, the ramped protrusions 244 have first angled releasable engagement surfaces 244*a* and second lock surfaces 244*b*, preferably at an angle to each other of ninety degrees or less. And the notched sections 242 have first angled releasable engagement surfaces 242*a* and second lock surfaces 242*b*, preferably at an angle to each other of ninety degrees or less. In this way, the second lock surfaces 242*b* of the notched sections 242 form a positive one-way lock with the second lock surfaces 244*b* of the ramped protrusions 244. So when the user pulls the sterility cap off the lancet 214 for use, the lancet's ramped protrusions 244 are not inadvertently pulled from engagement with the lancet control finger's notched sections 242.

FIGS. 13-18 show a lancing device 310 according to a fourth example embodiment of the invention that is similar to the third example embodiment just described. Thus, the lancing device 310 includes a housing 312, a control assembly 316 with control fingers 332 having notched sections 342 and angled retraction sections 340, and a lancet 314 having a body 318 and ramped protrusions 344. In this embodiment, however, the ramped protrusions 344 together are delta-shaped. Similarly to the third embodiment, the second lock surfaces 342*b* of the notched sections 342 form a positive one-way lock with the second lock surfaces 344*b* of the ramped protrusions 344 so that removing the sterility cap 326 does not pull the lancet's ramped protrusions 244 from engagement with the lancet control finger's notched sections 242.

In addition, the sterility cap 326 defines one or more stop surfaces 346 that extend beyond the dimension of the housing's lancing opening 324 to prevent the sterility cap from being inserted through the opening far enough to force the control assembly 316 back to the ready position. For example, the stop surfaces 346 may be defined by two or another number of wedge-shaped protrusions on the sterility cap 326.

Figure 13:
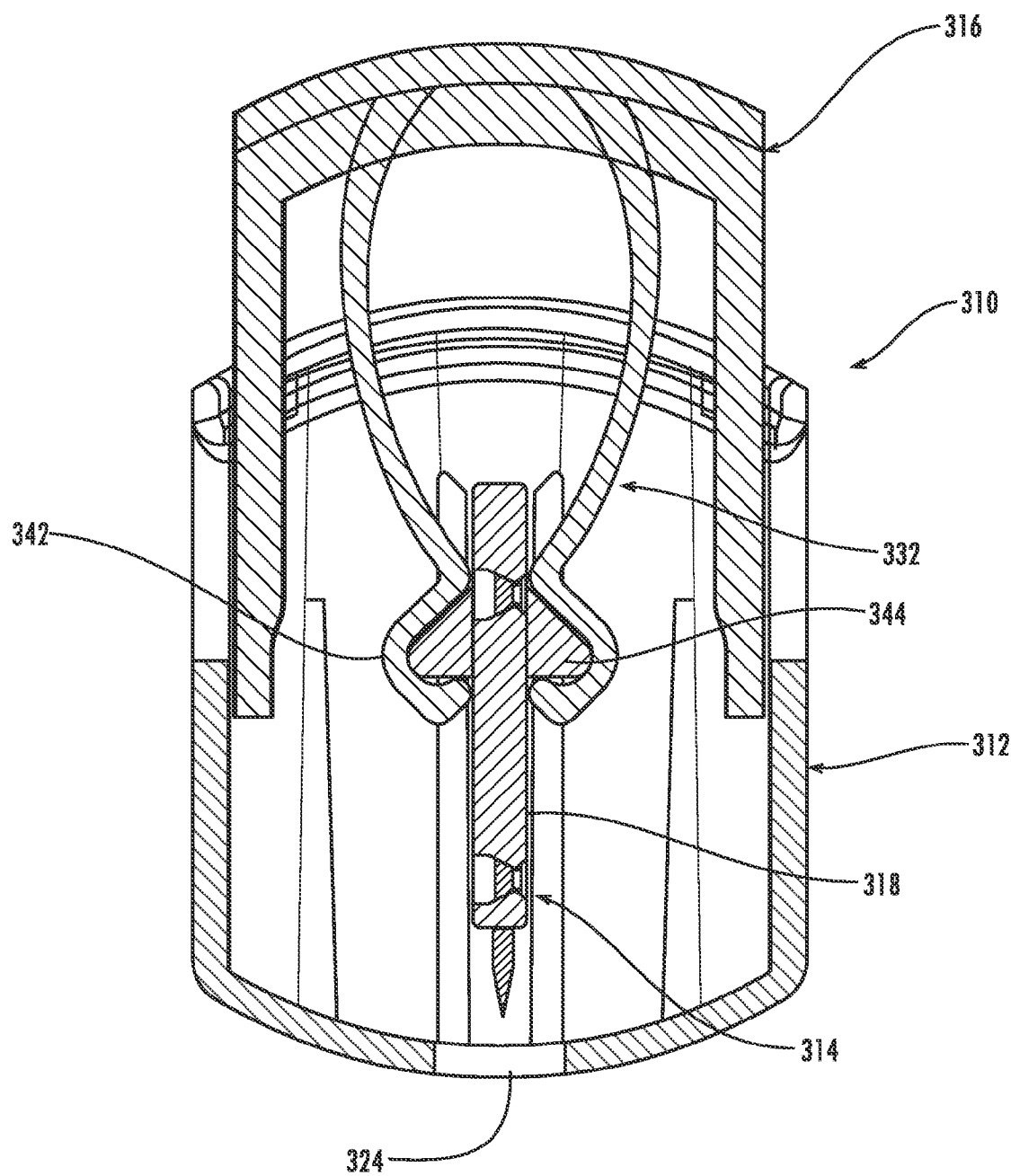
FIG. 13 is a side view of a lancing device according to a fourth example embodiment of the invention, showing the activation/retraction control assembly being pressed to activate the lancing device.
Figure 14:
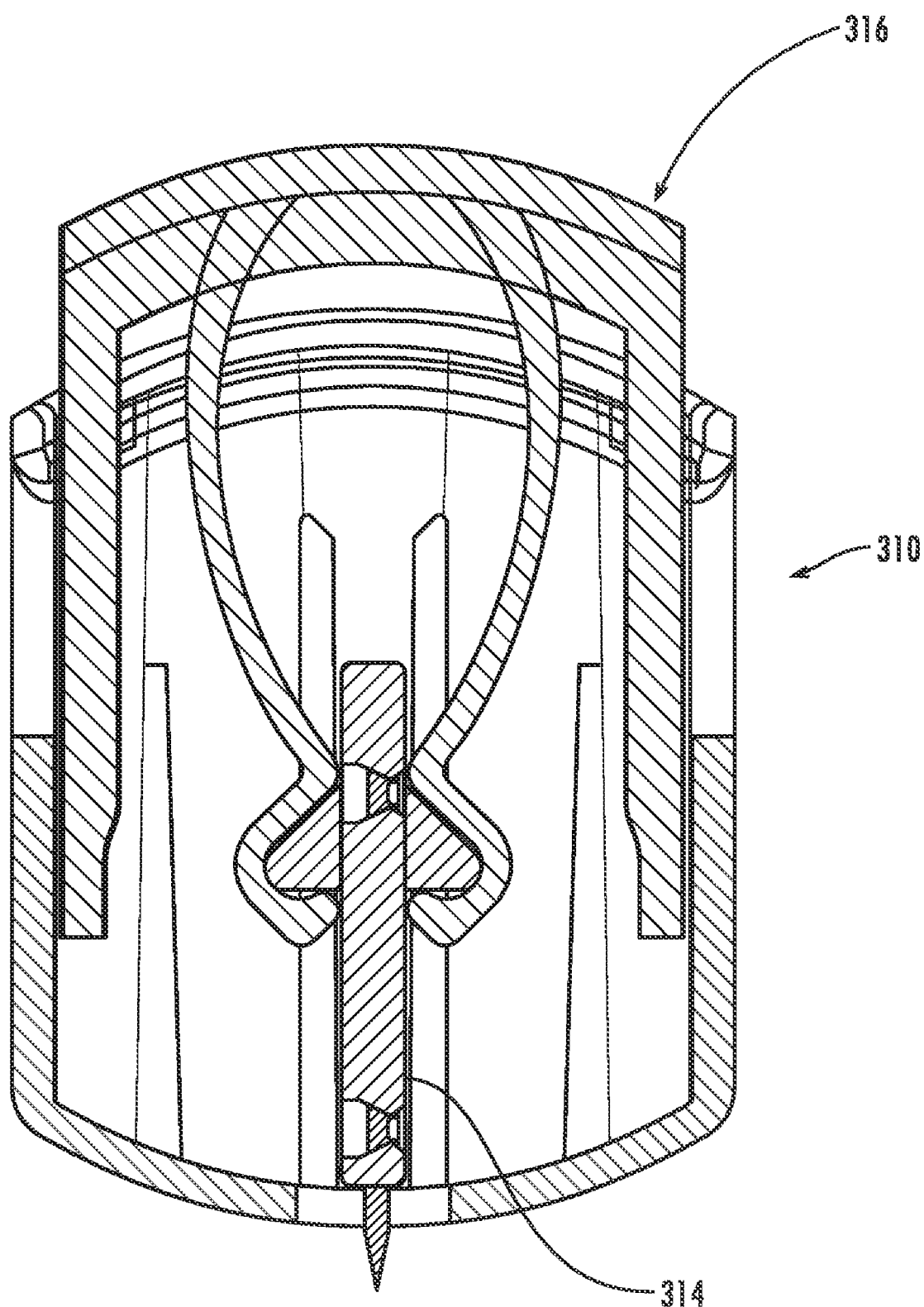
FIG. 14 is a side view of the lancing device of FIG. 13, showing the lancet stopped in a fully extended position for puncturing, and the activation/retraction control assembly free to disengage from the lancet and continue traveling forward.
Figure 15:
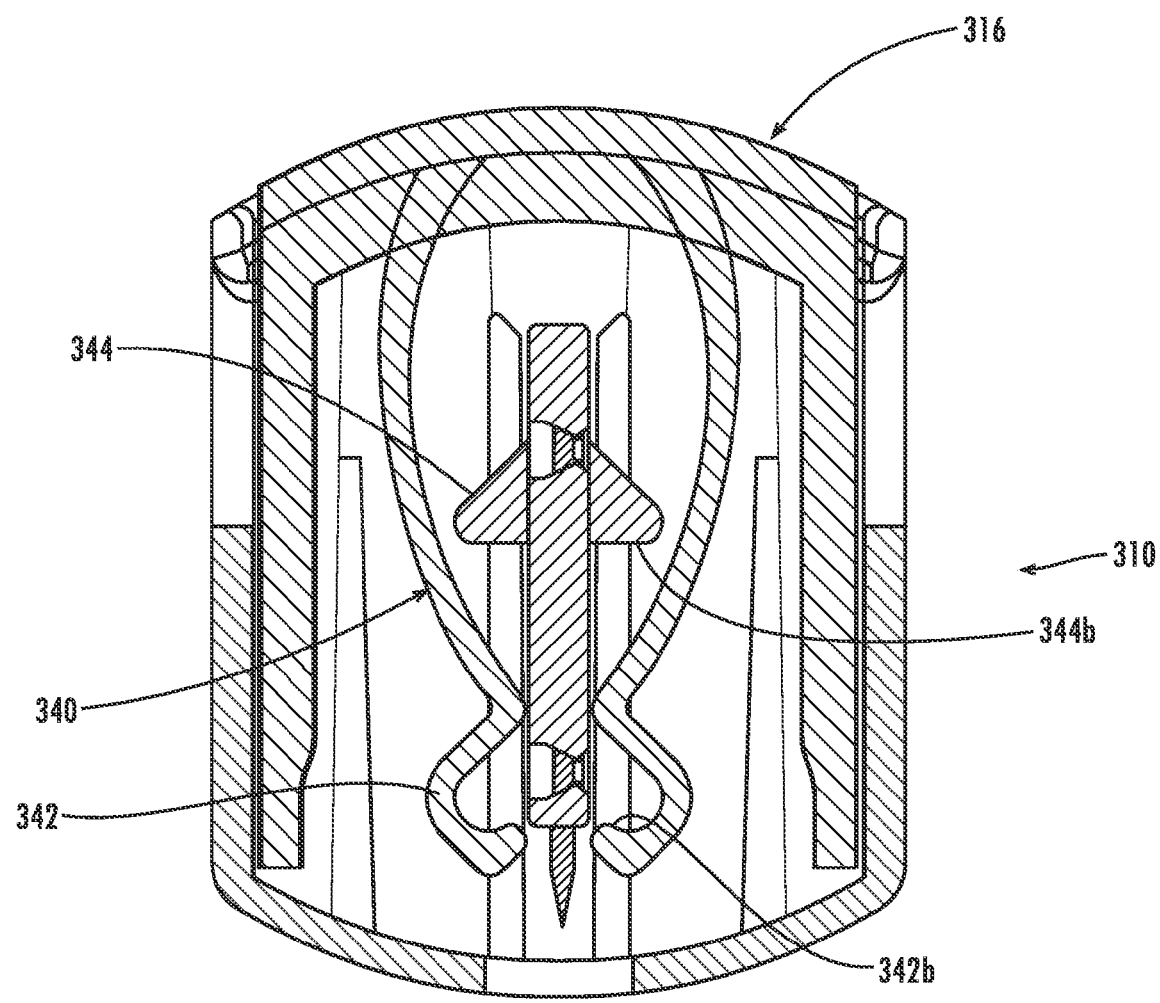
FIG. 15 is a side view of the lancing device of FIG. 13, showing the lancet, after being disengaged from the activation/retraction control assembly, now being retracted by the activation/retraction control assembly back into the housing.
Figure 16:
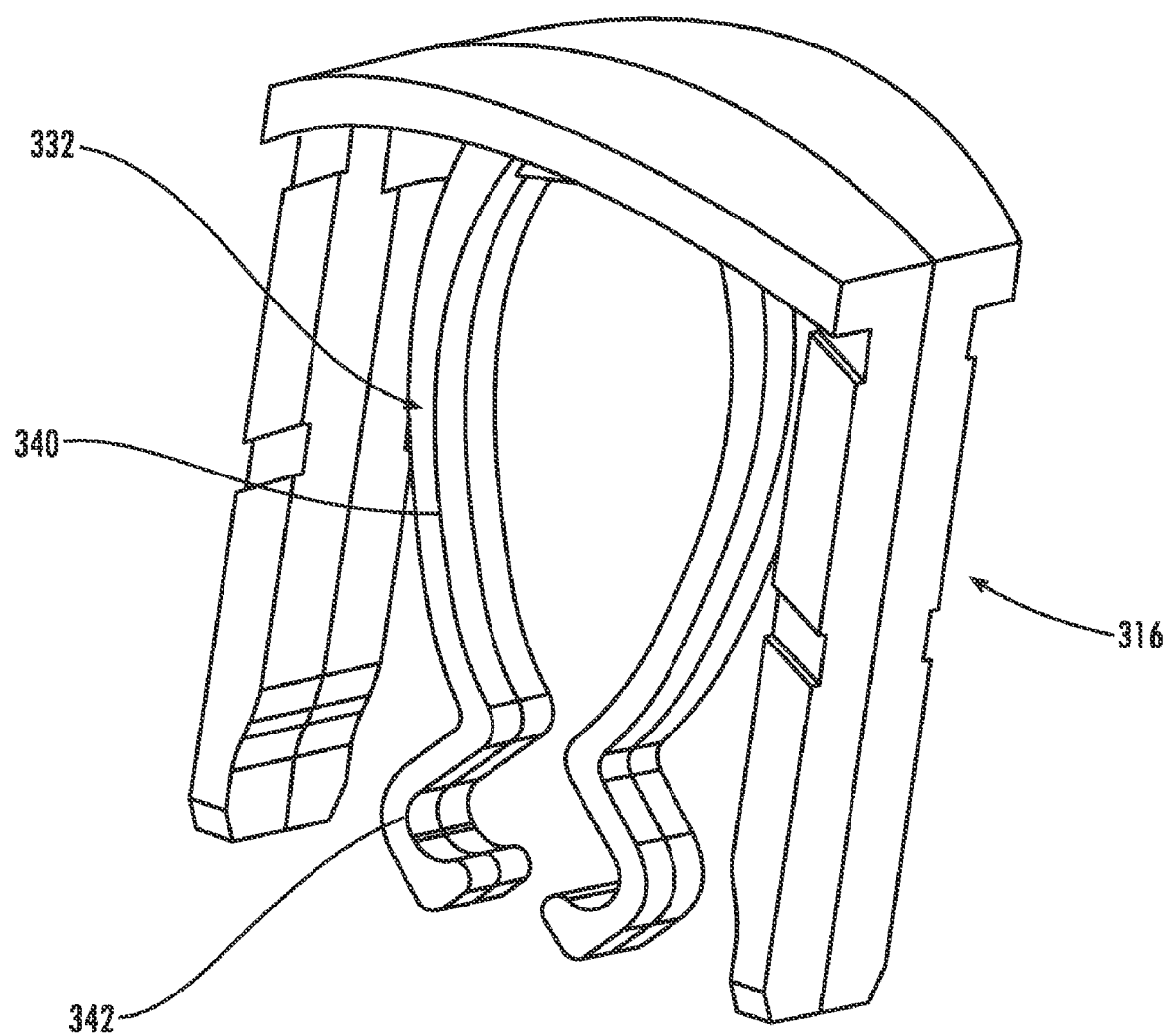
FIG. 16 is a perspective view of the activation/retraction control assembly of the lancing device of FIG. 13.
Figure 17:
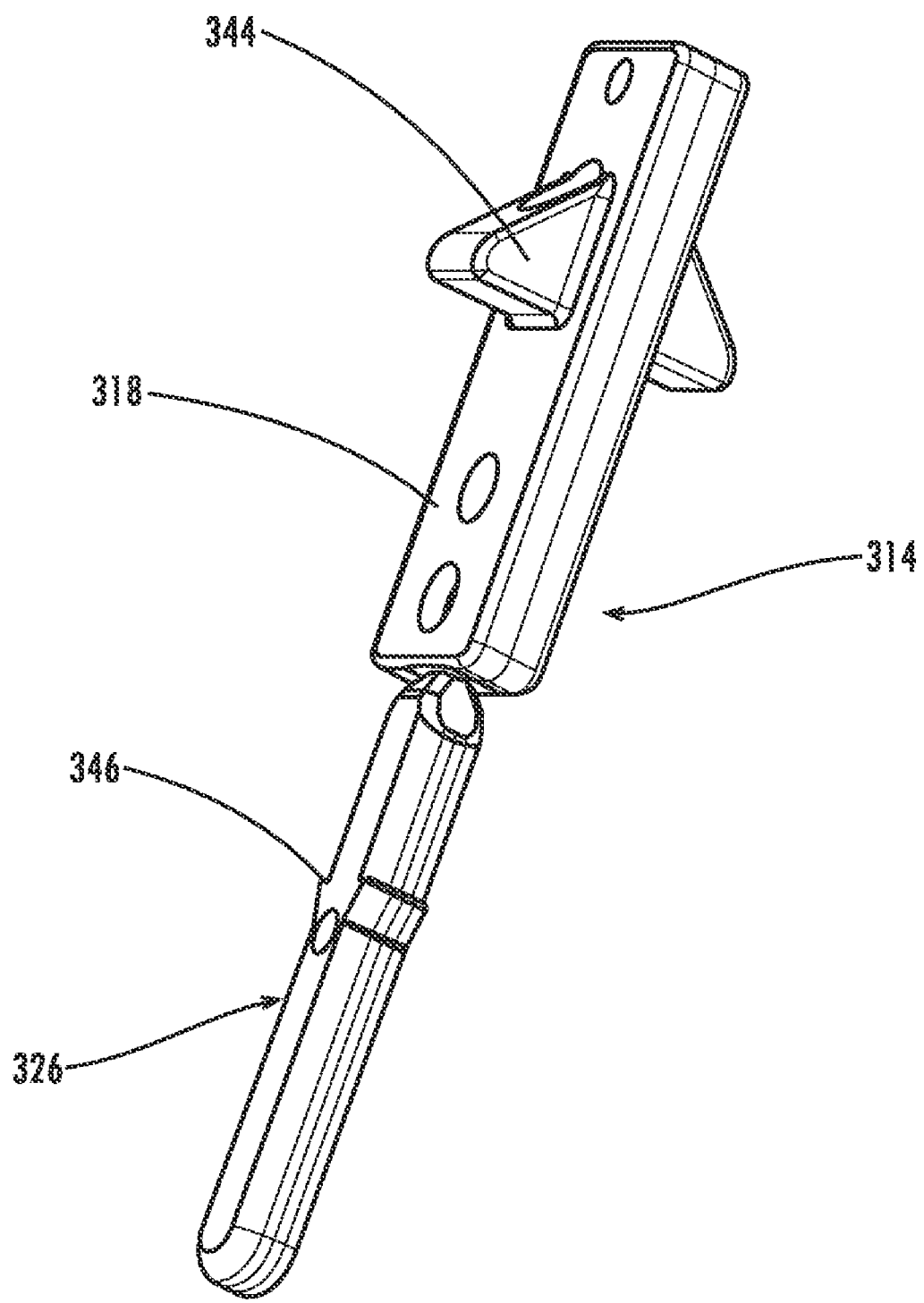
FIG. 17 is a perspective view of the lancet of the lancing device of FIG. 13.
Figure 18:
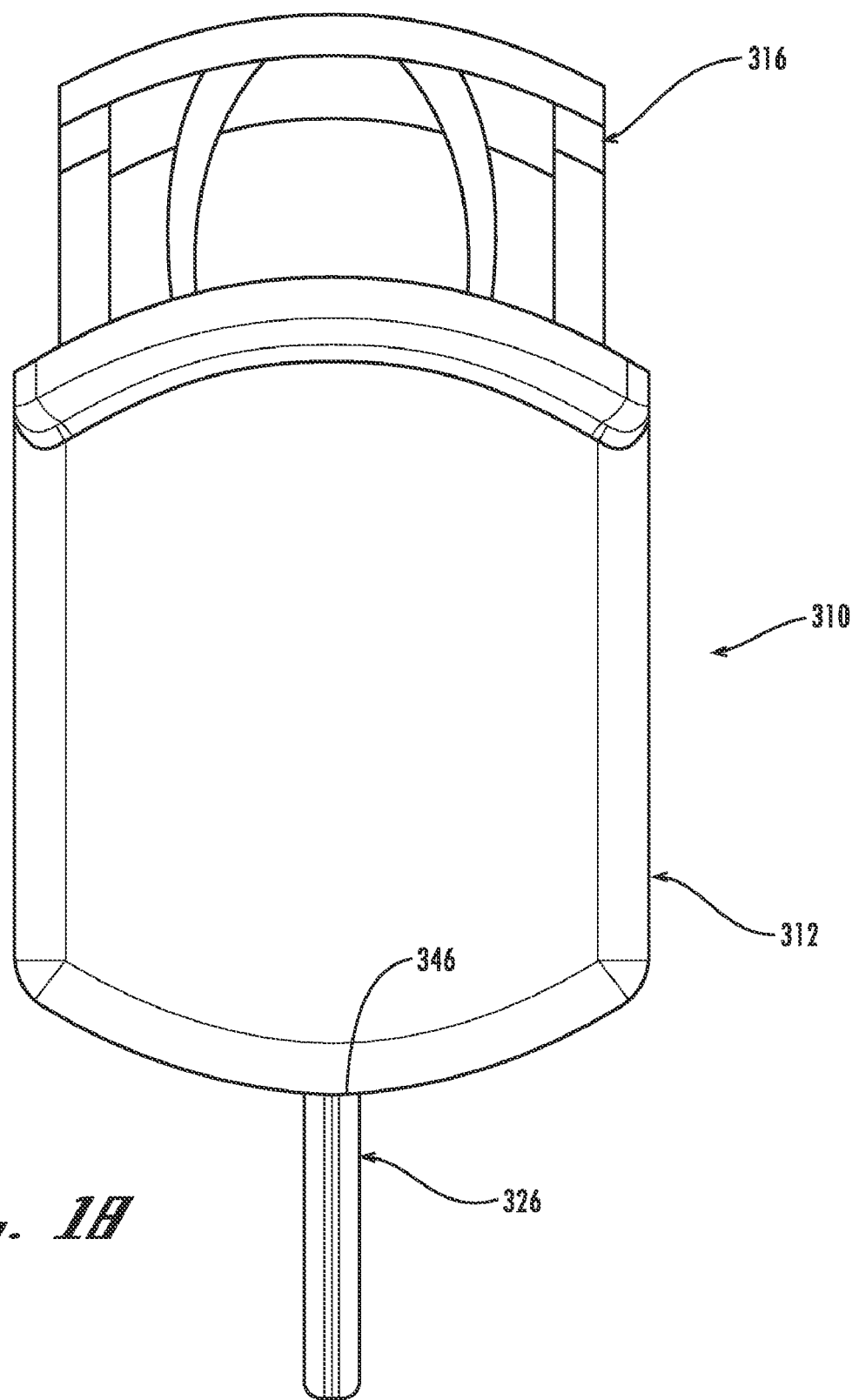
FIG. 18 is a side view of the lancing device of FIG. 13.

FIGS. 13-15 show the operation of the lancing device 310, which occurs in substantially the same fashion as the operation of the lancing device 10 of the first embodiment. In FIG. 13 the activation/retraction control assembly 316 being pressed to activate the lancing device. In FIG. 14 the lancet 314 is stopped in a fully extended position for puncturing, and the activation/retraction control assembly 316 is free to disengage from the lancet and continue traveling forward. And in FIG. 15 the lancet 314, after being disengaged from the activation/retraction control assembly 316, is now being retracted by the activation/retraction control assembly back into the housing 312.

In an alternative embodiment, the control assembly and the lancet are manufactured as a single integral piece, without the lancet-control assembly disengagement feature described herein, but with the detents or other cooperating engagement structures. And in another alternative embodiment, the lancing device is provided with a drive spring (without the detents or other cooperating engagement structures), but the control assembly and the lancet are provided with the cooperating releasable engagement structures.

While the invention has been described with reference to preferred and example embodiments, it will be understood by those skilled in the art that a variety of modifications, additions and deletions are within the scope of the invention, as defined by the following claims.

What is claimed is:

1. A lancing device, comprising:
   a housing comprising a guide structure and first engagement means;
   a lancet mounted within the housing in sliding engagement with the guide structure of the housing, the lancet having a lancet body, a puncturing tip extending therefrom and first and second protrusions on opposed sides of the lancet body, wherein the lancet travels through a lancing stroke from a ready position within the housing to a fully extended position with the tip extending out of the housing, and back to a retracted position within the housing;
   a control assembly comprising second engagement means for releasably engaging with the first engagement means of the housing, and releasing from engagement upon application of a threshold force to propel the lancet along the lancing stroke, the control assembly further comprising an opposed pair of resilient lancet control fingers, each of the lancet control fingers defining a notched section for releasably engaging one of the first and second protrusions of the lancet body, and an angled retraction section;
   wherein the opposed pair of resilient lancet control fingers flex to release the first and second protrusions of the lancet body from the notched sections thereof upon the lancet reaching the fully extended position, and the angled retraction section thereupon acts on the first and second ramped protrusions of the lancet body to retract the lancet tip back into the housing.

2. The lancing device of claim 1, wherein the first and second engagement means comprise interengaging detent elements formed in the housing and the control assembly.

3. The lancing device of claim 1, further comprising retention means for retaining the control assembly in a finished position after the control assembly is actuated to propel the lancet along the lancing stroke.

4. The lancing device of claim 1, wherein the first engagement means are configured so that the threshold force alone propels the lancet through the lancing stroke without a drive spring.

5. The lancing device of claim 1, wherein the first engagement means are configured so that the threshold force disengages the lancet from the control assembly when the lancet reaches the fully extended position.

6. The lancing device of claim 1, wherein the control assembly has a pressing member to which the threshold force is applied to activate the lancing device.

7. A lancing device, comprising:
   a housing having a guide channel along an interior face thereof, and first detent members;
   a lancet having a lancet body slidably mounted within the guide channel of the housing to traverse a lancing stroke, and a puncturing tip extending therefrom, wherein the lancet travels to a fully extended position with the tip extending out of the housing, the lancet body further comprising inclined ramped surfaces projecting from opposed sides of the lancet body, wherein each ramped surface comprises two obliquely angled surfaces; and
   a control assembly having an opposed pair of flexible fingers each defining a notched profile releasably engaging the inclined ramped surfaces of the lancet body and an angled retraction profile, the control assembly further comprising second detent members releasably engaging the first detent members of the housing, and wherein upon the application of a launch force the control assembly releases from engagement with the housing and is driven into the housing and drives the lancet to the fully extended position,
   wherein the notched profiles of the control assembly engage the ramped surfaces of the lancet body to hold the control assembly and the lancet together as the lancet travels toward the fully extended position, and when the lancet reaches the fully extended position the lancet disengages from the control assembly and the angled retraction profiles of the control assembly apply a retraction force on the lancet to retract the lancet into the housing.

8. The lancing device of claim 7, further comprising a set of cooperating engagement structures configured to hold the control assembly in a finished position disengaged from the lancet so that the control assembly does not move with the lancet when the lancet is being retracted.

9. A lancing device, comprising:
   a housing defining a guide channel and first releasable engagement structures;
   a lancet having a lancet body and a puncturing tip extending therefrom, wherein the lancet travels along the guide channel within the housing through a lancing stroke from a ready position to a fully extended position with the tip extending out of the housing and back to a retracted position within the housing, the lancet body further comprising first and second ramped protrusions projecting from opposite sides of the lancet body;
   a control assembly having second releasable engagement structures that cooperate with the first releasable engagement structures to releasably engage the housing until a threshold launch force is applied to the control assembly, the control assembly further comprising an opposed pair of flexing lancet control fingers, each defining a notched profile for releasably engaging one of the first and second ramped protrusions of the lancet body; and
   wherein upon application of the threshold launch force to the control assembly, the first releasable engagement structures disengage from the second releasable engagement structures and the launch force propels the lancet along the lancing stroke, the control assembly and the lancet being held together as the lancet travels toward the fully extended position, and when the lancet reaches the fully extended position the lancet disengages from the control assembly and the control assembly applies a retraction force on the lancet to retract the lancet into the housing.

10. The lancing device of claim 7, wherein each flexing lancet control finger includes an angled retraction section that biases the lancet to retract the lancet from the fully extended position.

* * * * *